United States Patent [19]

Zgoulli et al.

[11] Patent Number: 5,456,985
[45] Date of Patent: Oct. 10, 1995

[54] MICROCAPSULES OF OILY LIQUID

[76] Inventors: Slim Zgoulli, 19 Av. Marechal Juin, 5800 Gembloux; Philippe Delfosse, Rue Bois d'Avroy, 2B, 4000 Liege; Philippe Thonart, Reu Houlette, 20, 5850 Bovesse; Dominique Delacroix, 11 avenue des Ramiers, 1950 Kraainem, all of Belgium

[21] Appl. No.: 91,886

[22] Filed: Jul. 14, 1993

Related U.S. Application Data

[63] Continuation of Ser. No. 714,915, Jun. 13, 1991, abandoned.

[30] Foreign Application Priority Data

Jun. 13, 1990 [FR] France .................................. 90 07334

[51] Int. Cl.⁶ .............................. B32B 5/16; A61K 9/16; B01J 13/02
[52] U.S. Cl. .................................. 428/402.2; 428/402.21; 428/402.22; 424/490; 424/491; 424/493; 424/494; 424/496; 264/4.1; 264/4.3; 264/4.33
[58] Field of Search .................... 428/402.2, 402.21, 428/402.22; 424/490, 491, 493, 494, 496; 264/4.1, 4.3, 4.33

[56] References Cited

U.S. PATENT DOCUMENTS

| | | | |
|---|---|---|---|
| 3,116,206 | 12/1963 | Brynko et al. | 424/491 |
| 3,567,650 | 3/1971 | Bakan | 427/213.32 |
| 4,263,273 | 4/1981 | Appelgren et al. | 424/490 X |
| 4,895,725 | 1/1990 | Kantor et al. | 264/4.1 X |
| 5,008,254 | 4/1991 | Weibel | 514/57 |
| 5,013,557 | 5/1991 | Tai | 424/493 |
| 5,102,668 | 4/1992 | Eichel et al. | 424/494 X |

FOREIGN PATENT DOCUMENTS

| | | | |
|---|---|---|---|
| 122815 | 10/1984 | European Pat. Off. | 424/494 |
| 225303 | 6/1987 | European Pat. Off. | |
| 336662 | 10/1989 | European Pat. Off. | |
| 2415490 | 10/1074 | Germany | 424/494 |
| 007408 | 1/1982 | Japan | 424/494 |
| 2223943 | 4/1990 | United Kingdom . | |
| 81/02976 | 10/1981 | WIPO . | |

*Primary Examiner*—Shean Wu
*Attorney, Agent, or Firm*—Cooley Godward Castro Huddleson & Tatum

[57]  ABSTRACT

The present invention relates to micro-capsules constituted by a solid envelope consisting of a layer of coating materials including at least one gastro-resistant polymer, said solid envelope containing an oily liquid.

27 Claims, No Drawings

MICROCAPSULES OF OILY LIQUID

CROSS REFERENCE TO RELATED APPLICATIONS

This application is a Continuation of U.S. application Ser. No. 07/714,915, filed Jun. 13, 1991, now abandoned.

BACKGROUND OF THE INVENTION

The present invention relates to microcapsules, spherical microparticles, constituted by a jacket of a gastro-resistant coating material constituting the reservoir of an oily liquid that it contains.

The present invention also relates to a finished product in the form of a powder formed of microcapsules according to the invention providing a delayed release of an active principle of an oily nature.

Lastly the present invention relates to a method for the preparation of microcapsules and of a finished product in powder form according to the invention.

In therapeutics or in preventive medicine a need is frequently found for a technique enabling the release of an active principle after a prolonged stay in the organism.

In galenic pharmacy, the most frequent methods enabling these effects to be produced are: 1) Microencapsulation by coacervation with gastroresistant polymers (H. P. MERKLE and SPEISER, J. Pharm. Sci. 62:1444–1448 (1973); L. A. LUZZI and R. J. GERRAUGHTY, J. Pharm. Sci. 53:429–431 (1964); J. W. BEYGER and J. G. NAIRN J. Pharm. Sci. 75, 6:573–578 (1986). These methods are delicate to practise on an industrial scale and in addition often call for organic solvents which are the cause of toxic residues or call for the employment of amounts of substances which render the finished product economically uninteresting. 2) On the other hand, there exists another method equally very widespread, which enables formulations with delayed release to be obtained. This method is however only applicable to active principles in solid form [powder, granules, or tablets] and it consists of a coating [in a fluidized air bed or in a cyclone] by projection of a solution of enteric polymer onto cores suspended in a bed of hot air (H. C. CALDWELL and E. ROSEN J. Pharm. Sci. 53:1387–1391 (1964); M. J. ROBINSON, G. M. GRASS and R. J. LANTZ J. Pharm. Sci. 57:1983–1988 (1968); K. LEHMANN, D. DREHER, Pharm. Ind. 34:894–899 (1972); W. ROTHE, G. GROPPENBACHER Pharm. Ind. 34 (11a):892–894 (1972)

This technique is however not applicable when it is a matter of encapsulating an active principle directly in liquid form.

In the food industry, the technique of encapsulation of food oils, flavorings or colorings by polymers which are not gastro-resistant such as gum arabic, maltodextrin, gelatin, is very widespread. These applications are realized, in most cases, by the method of spraying or "spray drying" (ANANDARMAN, E. B. WILLIAM and G. REINECCIUS Perf. Flav. 8:49–56 (1983); K. IWAMI, M. HATTORI, S. NAKATANI and F. IBUKI, Agric. Biol. Chem., 51(12):3301–3307 (1987).

This technique for the preparation of microcapsules by drying by atomization has never been proposed and applied with gastro-resistant polymers in particular such as CAP or Eudragit R taking into account the actual practical difficulties. These polymers have in fact a tendency to be in thread form and to block the atomizer turbine taking into account their viscosity which is too high.

The patent EP 225 303 describes oil microcapsules which are prepared in aqueous emulsion in a solution of gastro-resistant polymers by the conventional technique of coacervation or by "spray-coating". The "spray-coating" technique is a technique of vaporization of the polymer onto a powder in a fluidized bed. The technique described in this patent relates to tablets, capsules or capsules which can contain oil prepared in two phases, coating by a gastro-resistant polymer only taking part after the preparation of the gelule or capsule proper.

The patent GB 2,223.943 also describes microcapsules. Here again it is a matter of gelules, particularly of gelatin, filled with oil which are only afterwards coated with a gastro-resistant polymer.

The patent EP 336 662 describes the preparation of microcapsules containing oil prepared in a first phase from an oil-in-water emulsion [oil/alginate] which is sprayed cold into a solution of $CaCl_2$, which causes precipitation of the polymer around the oil droplets. These microcapsules are then suspended in a solution of gastro-resistant polymer which is precipitated around the microcapsules by the addition of acid. It is hence a matter here also of an encapsulation technique by chemical coacervation.

It is an object of the present invention to obtain in original manner a gastro-resistant powder constituted by microcapsules comprising an oily liquid.

To do this, the present invention provides a method for the preparation of microcapsules constituted by a solid jacket of a coating material comprising at least one gastro-resistant polymer, said solid jacket containing an oily liquid, said method being characterized in that drying by atomization is carried out [also called spray-drying], by means of an atomizer, or an emulsion of the oil-in-water type obtained from said oily liquid and of an aqueous solution of the coating material comprising the one or more gastro-resistant polymers in admixture with at least one emulsifier.

In the present application, by coating material it is intended to denote polymers, including here gums or synthetic or natural resins, which are physiologically acceptable, or even proteins.

The present invention is based on physical encapsulation by direct atomization [drying] in a drying tower of an oil/water emulsion formed by the active principle and the aqueous solution of gastroresistant polymer in admixture with other conventional polymers so as to recover directly in one step a gastro-resistant dry powder, formed of microcapsules.

The method according to the invention therefore involves the operation of a device for drying by atomization. These devices are well known to the technicians skilled in the art. They are composed, for example, of a high tower at the top of which the liquid phase, in the event the emulsion, is finally dispersed by passage through a nozzle sprayer or rotary disk sprayer. The droplets formed pass through an air flow established in co- or in counter-current and taken to a controlled temperature particularly 140 degrees C. The microcapsules solidify and are recovered at the base of the spray chamber. The spraying is performed in a hot air current. The contact time of the microcapsules in the hot air is very brief and enables avoidance of the coated material from reaching a temperature higher than 40 degrees C. This method by atomization or nebulisation [spray-drying] offers the advantage of a very easy conversion to the industrial scale. The microencapsulation is formed in a single step and can be conducted continuously on large batches. According to the invention, it will be possible advantageously to use as the emulsifier a non-gastro-resistant conventional coating polymer that is to say endowed with filmogenic and emulsifying properties. None of the microcapsules described before the invention posesses an envelope constituted by a polymer with gastro-resistant properties in admixture with other polymers with emulsifying properties. According to the invention, to stablize the emulsion, it will be possible in addition, to use a non-ionic surface active emulsifier such as Tween 80®.

The polymers used in the method according to the invention are in the form of an aqueous solution which enables an emulsion of the oil-in-water type to be produced with the oily liquid. No organic solvent is hence used in the course of the manufacturing method which considerably reduces the risks during handling and also the presence of toxic residues in the finished products.

The appearance of the finished product obtained according to the method of the invention is a powder of which the sizes of the microcapsules constituting it is 25µ to 100µ. This appearance in the form of powder is particularly advantageous since it can be incorporated either in a formulation in solid form such as tablets, granules, dragees, or in a form to be dispersed in the liquid although the latter may be slightly acid, for example fruit juices, vegetable juices, lemonades.

Other atomization devices useful according to the invention are described, for example, in MARGARET M. L. "Spray drying of food flavors" Perfumer and Flavorist, 8, 49–56; YOUNG R. A. "Reviews the current situation for spray drying encapsulation" J. Foods Londres Janvier (86) p. 31–33, Spray drying encapsulation todays view; REINECCIUS G. A. et al. (1982) "Spray drying of Foods Flavors, J. theory of flavor retention" Perfumer and Flavorist, 7:4, 2–6. Among gastro-resistant polymers useful according to the invention, may be mentioned more particularly cellulose acetyl phthalate [CAP], cellulose acetotrimellitate [CAT], hydroxypropylmethyl cellulose phthalate [HP50 soluble at pH 5, HP55 soluble at pH 5.5] polyvinyl acetyl phthalate, a copolymer of methacrylic acid and acrylic acid such as products of the Eudraget brand, a latex prepared on the base of CAP such as products of the Aquacoat R, Aquateric R brand or again proteins such as giladins. The foregoing list is not exhaustive but illustrates the range of polymers which may be used to produce microcapsules according to the invention. Among useful non-gastro-resistant polymers endowed with emulsifying properties according to the invention, may be mentioned polysaccharide hydrocolloids such as gums, particularly gum arabic, guar gum, Karaya gum, carob gum, maltodextrins or again mixtures of the latter.

Here again, this list is not exhaustive but illustrates simply the range of polymers which may be used in admixture with a gastro-resistant polymer to produce microcapsules according to the invention. More particularly gum arabic, a polysaccharide of high molecular weight, may be mentioned whose principal skeleton is formed of D galactose, highly substituted by rhamnose arabinose groups and salified glucuronic acid groups [calcium, potassium, magnesium]. This hydrocolloid is soluble in water where it develops its properties: texturizing and anticrystallizing, emulsifying, filmogenic and adhesive.

Its usefulness of the same category as that of other gums mentioned above is double according to the present invention:—emulsifying agent for development of an oil/water type emulsion—an encapsulating agent used on oils. In addition there is no limit to the admissable daily doses.

The maltodextrins are obtained by hydrolysis of the starch molecule by a method identical with the preparation of glucose syrups. Starch is a polymer of D-glucose, the linear chains are obtained by 1–4 linkages, the branch chains by linkages of 1–6. The starch molecule degraded by hydrolysis to a more or less advanced stage gives a glucose syrup which will be characterized by the measurement of dextrose equivalent [D.E.].

The maltodextrins DE 20 [glucose syrup] are white powders, soluble in the cold in water, they give solutions of little viscosity. Used in equal proportion with gum arabic for their film forming and encapsulating properties, they enable the viscosity of the polymer solution to be kept at a fairly low level.

In one embodiment, it is possible to use a certain amount of plasticizers in the polymer solution. There may mentioned 1) Triacetin [glycerin triacetate] is a liquid of density of 1.15 and a boiling point of 259 degrees C. It is soluble in 14 parts of water, in alcohol, benzene, chloroform and ether. 2) Propyleneglycol is a clear, colorless, odorless liquid of slightly sweet taste, hygroscopic. It is water miscible. 3) Cetanol These plasticizers are used at concentrations varying between 10 and 30% of the weight of the coating polymers, they contribute to the flexibility of the film after drying and facilitate the atomization of the emulsion.

In a particular embodiment of the method, the material therefore comprises as a plasticizer triacetin, propyleneglycol or cetanol.

The plasticizer may be used at a concentration varying between 10 and 30% of the weight of the coating material.

Prior to the formation of the emulsion, the solubilisation of the polymers in water is performed if necessary.

By way of gastro-resistant polymer, cellulose acetylphthalate [CAP] is preferably used.

Cellulose acetylphthalate [CAP] is a derivative of cellulose, with acetyl groups and phthalate acid which here are substituted; it is soluble in water, from pH values higher than 5.7. It is insoluble in an acid medium which confers on it its gastro-resistant properties.

According to the invention, it will be advantageously useful in the form of an aqueous solution of 5 to 20%, for example 10% [w/w], into which will be added 3 to 10%, for example 5.6% of ammonia [w/w with the respect to the polymer] to stablize it. Any ammonia is removed by evaporation during the atomization; in the case where residues would be present in the finished product, it is possible to neutralize the latter by washing of the powder with acid.

When the gastro-resistant polymer is cellulose acetylphthalate, the latter is hence solubilized in an aqueous solution at a pH of at least 5.7, for example, from 5.7 to 10.

Generally, the gastro-resistant polymer, particularly cellulose acetylphthalate can be used in the form of a 5 to 20% aqueous solution, in particular 10% [w/w] in a proportion varying between 5 and 15%, preferably between 3 and 8% of dry matter in the emulsion.

The one or more non-gastro-resistant polymers have emulsifying properties, particularly gum arabic and the maltodextrins will advantageously be used so as to reach a final concentration of polymer of 5 to 30%, in particular 15% of dry matter in the emulsion.

The total dry matter in the emulsion corresponds also to the weight of the microcapsule obtained.

According to one embodiment of the method according to the invention, the first mixture of one or more coating polymers a second mixture of the oily liquid to be encapsulated with the non ionic surfaceactive emulsifier as the case may be, is produced and then said first and second mixtures are mixed together and finally plasticizer added as necessary.

The amount of oily liquid engaged in the method would generally represent about 20 to 50%, in particular 30% of the total dry matter in the emulsion.

The non-ionic surface-active emulsifier used in the method will preferably be Tween 80®, for example in a proportion of 0.1 to 1%, in particular 0.5% (weight/weight) of the emulsion.

By way of oily liquid, it is possible, by the method according to the invention, to encapsulate a wide range of oils of various origins saturated or unsaturated, or mixtures of fatty acid or of triglycerides.

In particular, it will be possible to encapsulate food oils recommended by doctors and nutritionists, particularly in order to prevent cardiovascular disorders, such as peanut oil, fish oil rich in unsaturated fatty acids of the (n-3) family (stearidonic eicosapentaenoic and docosahexaenoic acids). There may also be mentioned borage oil rich in gamma-linolenic acid and other unsaturated fatty acids of the family (n-6) which enable the deficiencies of the enzymatic equipment of synthesis of the icosanoids to be offset.

Finally, will be mentioned mixtures of free fatty acids rich in interesting fatty acids, by an enzymatic hydrolysis method which is described in the example of patent FR 89 12980.

In a preferred embodiment in the method according to the invention, the polyunsaturated fatty acids contained in the oily liquid are derived from acids alpha-linolenic and linoleic essential fatty acids. It is preferentially gamma-linolenic acid, arachidonic acid, docesatetraenoic acid, docosapentaenoic acid, stearidonic acid, eicosapentaenioic acid, and docosahexaenoic acid.

All the oils containing naturally one or several essential polyunsaturated fatty acids in free form or in the form of glyceride, are hence particularly suitable. Among the latter, may be mentioned in particular fish oils, such as sardine and cod for the polyunsaturated fatty acids of the family (n-3), and oils from boraga DPO or from blackcurrant seeds, for the essential polyunsaturated fatty acids of the family (n-6).

The encapsulated oily liquid product may contain any active principle that it is desired to introduce into the organism at the level of the intestine, as long as it is liposoluble. There may be mentioned for example vitamins A, D, E and K, coloring agents, antibiotics, but also peptides of interest. There may be mentioned more especially the active principles whose intestinal absorption is facilated by their association with an oil.

It will be noted that, in the case where the oily liquid or the active principle has a disagreable taste or smell, this is the case, for example, with fish oil, the coating masks the latter during administration at the level of the mouth, but also the envelope being gastro-resistant, it prevents its release at the level of the stomach and thereby, disagreable tastes during digestion.

The encapsulation protects the active principle from oxidation, which permits simplified and prolonged storage of the product. To increase this effect, the oily active principle may be mixed with vitamin E (alpha-tocopherol), this is a liposoluble antioxidant. As has been seen, the atomization process used according to the present invention, has the advantage of only exposing the finished product to a high temperature for a very short time (some seconds) which also reduces the risk of oxidation of the active principle.

The microcapsules obtained by the method according to the invention are novel and it is therefore an object of the invention to provide microcapsules by way of novel products, characterized by a solid envelope consisting of a layer of coating material comprising at least one gastro-resistant polymer, said solid envelope containing an oily liquid; and in particular the micro-capsules can be characterized in that they are constituted, in a particular embodiment, by a gastro-resistant polymer in admixture with one or more non-gastro-resistant coating polymers with emulsifying properties.

Other characteristics and advantages of the present invention will appear in the light of the detailed example which follows.

EXAMPLE 1: ATOMIZATION OF AN OIL IN EMULSION IN A SOLUTION CAP, MALTODEXTRIN, GUM ARABIC AND TRIACETYL OR POLYPROPYLENEGLYCOL

1) Material

| | |
|---|---|
| gum arabic: spray cleaned | (FEDERA) |
| maltodextrin DE (20) | (VEL) |
| cellulose acetyl phthalate: (CAP) | (EASTMAN) |
| fish oil | (ORTIS) |
| Tween 80 | (FEDERA) |
| propyleneglycol | (FEDERA) |
| triacetin | (JANSSEN) |
| Ultra Turrax-T25 mixer | (IKA VAN DER HEYDEN) |
| Atomiser (Mobil Mixer Spray Dryer) | (NIRO ATOMISER) |

2) Methods 2.1.) Composition of the emulsions

The percentages are meant in ratio weight/weight of the products in emulsion, the rest being constituted by distilled water.

TABLE 1

| % by weight Examples | CAP (%) | Gum arabic (%) | MD20 (%) | Plasticiser (%) | Oil +0.5% Tween80 (%) | DM (%) | Water (%) |
|---|---|---|---|---|---|---|---|
| n° 1 | 7 | 8 | — | — | 6.6 | 21.6 | 78.4 |
| n° 2 | 7 | 4 | 4 | — | 7.5 | 22.5 | 77.5 |
| n° 3 | 7 | 4 | 4 | 1.5(T) | 7.5 | 24.0 | 76 |
| n° 4 | 8 | 3.5 | 3.5 | 1.5(T) | 7.5 | 24.0 | 76 |
| n° 5 | 8 | 3.5 | 3.5 | 3.0(T) | 7.5 | 25.5 | 74.5 |
| n° 6 | 8 | 3.5 | 3.5 | — | 7.5 | 22.5 | 77.5 |
| n° 7 | 8 | 3.5 | 3.5 | 3.0(PG) | 8.0 | 26.0 | 74.0 |

MS: dry matter in the emulsion
MD20: maltodextrin DE 20 (glucose syrup)
T: triacetin
PG: propyleneglycol 2.2) Procedure Disperse CAP in a 5% ammoniacal solution by stirring for 45 minutes (solution 1).

Disperse the gum arabic; magnetic stirring for 30 minutes; heat to 45° C. (solution II).

Add the amount of Maltodextrin DE 20–23 to the solution II, stirring for 20 minutes (solution III).

Mix the solutions I and III, and leave under stirring for 20 minutes.

Add the oil-Tween 80 mixture to the polymer solution; still with magnetic stirring.

Add the plasticizer stirring vigorously.

2.3) Formation of the emulsion

The emulsions are formed by use of an Ultra-Turrax mixer and on an amount of sample varying between 400 and 500 g.

Thus, for example no. 3, the amounts of the different constituents engaged in the process may be:

| Ingredients | weight | in % |
|---|---|---|
| Gum arabic | 16 g | 4.0% |
| Maltodextrin DE20 | 16 g | 4.0% |
| Cellulose acetylphthalate: CAP 7.0% | 28 g | |
| Fish oil +0.5% Tween 80 | 30 g | 7.5% |
| Triacetin | 6 g | 1.5% |
| 5% solution of NH$_4$OH | 240 g | 60.0% |
| Distilled water | 64 g | 16.0% |
| | 400 g | 100.0% |

In order to limit heating of the product during emulsification, the vessel containing the product is plunged an ice bath. The optimum emulsification speed is 24,000 rpm, with a mixer head for fine dispersion (S25N-25F), for 20 minutes.

2.4) Evaluation of the emulsion a) measurement of the turbidimetric index:

an amount of 50 ul of emulsion is diluted in 25 ml of a 1% SDS solution (Sodium Dodecyl Sulfate) to avoid coalescence during the measurement.

the measurement of the optical density at 500 nm.

$$T = \frac{2,303 \, A}{L} \, (m^{-1}) \quad \begin{array}{l} A = \text{optical density} \\ L = \text{thickness of the cell} \end{array}$$

b) observation under the microscope

The microscopic method enables the fineness and quality of an emulsion to be evaluated directly, by estimation of the size of the droplets.

2.5) Drying by atomization

Preparation of the drying chamber: after cleaning and disinfection of the chamber, the machine is put into operation about ½ hour before the start of atomization. This time lapse enables the desired temperature to be reached inside the chamber and the sound rotation of the turbine via the control of the air pressure.

Temperature: by means of probes placed at the input and the outlet of the chamber it is easy to control the output temperature variation between these two points at any moment.

Before atomization, once the chamber is dry and it has reached the desired temperature, it is advisable to start by injection of distilled water in the atomizer. At this moment, a drop in the output temperature is observed due to evaporation of the water inside the chamber. It is easy to control the output temperature by varying the flow rate of the injected liquid.

Once the temperature is stabilized, after about 10 minutes injection of the emulsion can be started.

The atomization conditions are as follows:

Flow rate of the liquid: ml/min

Compressed air pressure: 6 bars (30,000 rpm).

Input temperature: 140° C.

Output temperature: 80°–85° C.

The powder is collected in a vessel fixed to the base of the cyclone.

2.7) Determination of the oil a) Extraction of the oil at the surface:

Hexane is used to extract the oil at the surface from the microcapsules.

3 g of microcapsules are weighed into a test tube, 25ml of hexane PA are added and it is stirred for two hours [a rotary stirrer].

Then, it is filtered under vacuum, the powder is washed by 3 times 8 ml of hexane. The eluate is recovered in a ground-stoppered flask, calibrated and then the solvent evaporated with the rotavapor.

b) Gastro-resistance:

A test sample of 3 g of microcapsules was taken, washed with hexane and placed into 20 ml of 0.1 N HCl with stirring and in a water bath at 37° C. After two hours incubation a centrifugation is carried out at 20,000 rpm for 20 minutes. The supernatant liquid is recovered, and twice 20 ml of acetone were added thereto. The acetone having caused the precipitation of the gum arabic and of the maltodextrin, the liquid phase was taken up after decantation. The recovered fractions were extracted with twice 20 ml of hexane in a separating funnel, the organic phase was dried on the rotavapor. After evaporation, the liberated oil was weighed.

The reasons for the choice of acetone and of hexane for extraction of the oil after incubation are summarized in three points:

Acetone is miscible both with oil and with water, there is only a single phase.

Acetone precipitates the encapsulating agent [gum arabic and maltodextrin] after extraction of the oil, the separation of the liquid-solid phases can be done by decantation.

The hexane precipitates the CAP and the plasticizers, it is miscible with acetone and fish oil.

The results in percentage of oil salted out into the 0.1N HCl bath after 2 hours at 37° C., with respect to the total theoretical weight of oil in the powder are shown in Table 6.

TABLE 6

| Examples | % of Oil Salted Out |
|---|---|
| 1 | 8.0% |
| 2 | 3.6% |
| 3 | 3.3% |
| 4 | 1.0% |
| 5 | 2.18% |
| 6 | 3.2% |
| 7 | 3.8% |

3) Results 3.1) Study of the Emulsion

The determination of the size of the globules is a reliable way of evaluating emulsification and consequently, the characteristics and stability of the emulsions.

The microscopic method enables the observation, the counting, and the measurement of the size of the globules, and the turbidimetric index is inversely proportional to the size of the droplets.

a) Measurement of the turbidimetric index as a function of the time of emulsification.

The measurements are shown in table 2.

TABLE 2

| Emulsification time | Optical density | Turbidity |
|---|---|---|
| 10 | 0.132 | 0.303 |
| 15 | 0.145 | 0.333 |

TABLE 2-continued

| Emulsification time | Optical density | Turbidity |
| --- | --- | --- |
| 20 | 0.153 | 0.352 |
| 25 | 0.154 | 0.354 |

In theory, the increase in emulsification time causes the reduction in the size of the droplets. The minimum time necessary for obtaining globules of a sufficiently small size is under our conditions 20 minutes. The size of the droplets, after measurement by microscope is situated between 2μ and 10 μm.

b) Measurement of the turbidimetric index is a function of the shearing speed of the Mixer. The results are shown in Table 3.

TABLE 3

| Speed rpm | Optical density | Turbidity |
| --- | --- | --- |
| 9400 | 0.125 | 0.287 |
| 13000 | 0.176 | 0.405 |
| 20000 | 0.276 | 0.626 |
| 24000 | 0.272 | 0.677 |

The increase in energy absorbed by the solution facilitates the fineness and stability of the emulsion, until the droplets reach a minimum size, after which the supplementary addition of energy can lead to over-emulsification.

c) Measurement of the turbidimetric index as a function of the concentration of Tween 80 The results are shown in table 4.

TABLE 4

| % of Tween/oil | Optical density | Turbidity |
| --- | --- | --- |
| 0.00% | 0.240 | 0.552 |
| 0.05% | 0.390 | 0.898 |
| 0.10% | 0.444 | 1.022 |
| 0.20% | 0.456 | 1.050 |

The surface-active agent function of the Tween 80 reinforces the cohesion of the film by surrounding the oil globules in emulsion. An encapsulating agent is used which possesses also emulsifying properties like gum arabic, the addition of Tween 80 in very small amount reinforces the stability of the emulsion and gives the film very great tear strength.

d) Conclusion The fineness of the emulsion depends on:
the shearing speed of the apparatus used for the emulsification process,
the duration of the emulsification,
the concentration of the surface-active agent, 3.2) Determination of the Oil at the Surface The results are shown in Table 5:

TABLE 5

| Examples | % Oil at the Surface |
| --- | --- |
| 1 | 7% |
| 2 | 6.5% |
| 3 | 5.7% |
| 4 | 4% |
| 5 | 6.5% |
| 6 | 7% |

TABLE 5-continued

| Examples | % Oil at the Surface |
| --- | --- |
| 7 | 8% |

A very low ratio of oil at the surface is observed, which can be explained in two ways:
droplets of oil of small size facilitate the formation of sealed microcapsules,
in the range of temperature studied, an input temperature of 140° C. seems a good compromise between a good yield of encapsulation, sufficient rapidity of drying and a good quality of finished product.

We claim:

1. Microcapsules comprising:
(1) a solid envelope consisting of a layer of coating material comprising at least one gastro-resistant polymer in admixture with one or more non-gastro-resistant coating polymers with emulsifying properties, and
(2) an oily liquid contained in said solid envelope, wherein said gastro-resistant polymer is selected from the group consisting of cellulose acetyl phthalate, cellulose hydroxypropylmethyl phthalate, polyvinyl acetyl phthalate, a copolymer of a methacrylic acid and an acrylic acid, and a gliadin protein and wherein said microcapsules are from about 25 microns to about 100 microns in size.

2. Microcapsules according to claim 1, wherein said non-gastro-resistant polymer is a polysaccharide hydrocolloid.

3. Microcapsules according to claim 2, wherein said non-gastro-resistant polymer is a mixture of gum arabic and maltodextrins.

4. Microcapsules according to claim 1, wherein the coating material comprises a mixture of cellulose diacetyl phthalate, gum arabic and maltodextrins.

5. Microcapsules according to claim 1, wherein the coating material further comprises a plasticizer.

6. Microcapsules according to claim 5, wherein said plasticizer is triacetin, propylene glycol, or cetanol.

7. Microcapsules according to claim 5, wherein said plasticizer is between about 10 to about 30% weight/weight of the total weight of the coating material.

8. Microcapsules according to claim 5, wherein the coating material comprises a mixture of cellulose acetyl phthalate, maltodextrin, gum arabic, and said plasticizer.

9. Microcapsules according to claim 8, wherein said plasticizer is triacetin or propylene glycol.

10. Microcapsules according to claim 1, wherein said oily liquid comprises a polyunsaturated oil of animal or vegetable origin.

11. Microcapsules according to claim 10, wherein said oil contains a polyunsaturated fatty acid comprising free alpha-linolenic acid or linoleic acid or a triglyceride thereof.

12. Microcapsules according to claim 11, wherein said polyunsaturated fatty acid is derived from an essential alpha-linolenic acid of the n-3 family, an alpha-linoleic acid of the n-6 family, or a trigyceride enriched in said acid.

13. Microcapsules according to claim 1, wherein said oily liquid contains a liposoluble active principle.

14. Microcapsules according to claim 1, wherein said microcapsules are in the form of a powder.

15. A method for preparing a microcapsule comprising (1) a solid envelope consisting of a layer of coating material comprising at least one gastro-resistant polymer in admixture with one or more non-gastro-resistant coating polymers with emulsifying properties, and (2) an oily liquid contained in said solid envelope, said method comprising:

drying by atomization without organic solvents an oil-in-water emulsion obtained from said oily liquid and an aqueous solution comprising polymers of said coating material wherein at least one gastro-resistant coating polymer is in admixture with at least one emulsifier whereby microcapsules of between about 25 microns and about 100 microns are produced.

16. The method according to claim 15, wherein said emulsifier is a non-gastro-resistant coating polymer.

17. The method according to claim 15, wherein said emulsifier comprises a non-ionic surface-active emulsifier.

18. The method according to claim 15, wherein said oil-in-water emulsion comprises fine droplets of between about 2 and about 10 microns in diameter.

19. The method according to claim 15, wherein said aqueous solution comprises about 5 to about 20% by weight of said coating polymers, and wherein the total dry matter of said oil-in-water emulsion comprises about 5 to about 30% by weight of one or more of said coating polymers, with about 5 to about 15% by weight being said gastro-resistant coating polymer.

20. The method according to claim 19, wherein said aqueous solution of coating polymers comprises a gastro-resistant coating polymer which is cellulose acetyl phthalate solubilized in said aqueous solution at a pH of at least 5.7, and wherein said gastro-resistant coating polymer is in the form of a 10% aqueous solution constituting between about 3 and about 8% weight/weight of said dry matter in said oil-in-water emulsion.

21. The method according to claim 20, wherein said aqueous solution of coating polymers comprises about 5.6% of ammonia with respect to the weight of said coating polymers.

22. The method according to claim 15, wherein gum arabic and maltodextrins are used in about equal proportions and the total concentration of non-gastro-resistant coating polymer in said dry matter of the oil-in-water emulsion is about 15%.

23. The method according to claim 15, comprising preparing a first mixture of said polymers of said coating material and a second mixture of said oily liquid for encapsulation, mixing said first and second mixtures together optionally with a non-ionic emulsifier to form an oil-in-water emulsion and optionally adding a plasticizer to the emulsion.

24. The method according to claim 23, wherein the amount of said oily liquid represents about 20 to about 50% of the total dry matter in said oil-in-water emulsion.

25. The method according to claim 15, wherein said emulsifier is about 0.1 to about 1% weight/weight proportion of the total dry matter in said oil-in-water emulsion.

26. The method according to claim 15, wherein said drying is performed by atomization with an atomizer whose input temperature is about 140° C.

27. Microcapsules prepared according to the method of claim 15.

* * * * *